US006612308B2

(12) United States Patent
Fisher et al.

(10) Patent No.: US 6,612,308 B2
(45) Date of Patent: Sep. 2, 2003

(54) PORTABLE ISOCAPNIA CIRCUIT AND ISOCAPNIA METHOD

(76) Inventors: Joseph Fisher, 603 Clarke Avenue West, Unit 21, Thornhill, Ontario (CA), L4J 8P9; Alex Vesely, P.O. Box622, Station "Q", Toronto, Ontario (CA), M4T 2N4; Hiroshi Sasano, 3-295 Oobari Meitou-ku, Nagoya, Aichi 465 0064 (JP); Steve Iscoe, Department of Physiology, Botterell Hal Room 439, Queen's University, Kingston, Ont. (CA), K7L 3N6; Alex Stenzler, 771 Terraine Ave, Long Beach, CA (US) 90804

( * ) Notice: Subject to any disclaimer, the term of this patent is extended or adjusted under 35 U.S.C. 154(b) by 0 days.

(21) Appl. No.: 10/093,797

(22) Filed: Mar. 8, 2002

(65) Prior Publication Data

US 2003/0000525 A1 Jan. 2, 2003

Related U.S. Application Data

(63) Continuation-in-part of application No. 09/676,899, filed on Oct. 2, 2000.

(30) Foreign Application Priority Data

Mar. 31, 2000 (CA) ................................ 2304292
Mar. 12, 2001 (CA) ................................ 2340511

(51) Int. Cl.$^7$ ................................ A62B 7/00

(52) U.S. Cl. ..................... 128/205.11; 128/203.12

(58) Field of Search .......... 128/204.18, 204.21–204.23, 128/204.26, 204.28, 204.29, 205.11, 205.13–205.17, 205.24, 200.22, 200.24, 203.12, 203.13, 203.28, 205.18, 910

(56) References Cited

U.S. PATENT DOCUMENTS

| 3,901,230 | A | * | 8/1975 | Henkin | 128/205.17 |
|---|---|---|---|---|---|
| 3,921,628 | A | * | 11/1975 | Smythe et al. | 128/204.21 |
| 4,188,946 | A | | 2/1980 | Watson et al. | |
| 4,991,576 | A | * | 2/1991 | Henkin et al. | 128/203.28 |
| 5,320,093 | A | * | 6/1994 | Raemer | 128/203.12 |
| 5,398,675 | A | * | 3/1995 | Henkin et al. | 128/203.12 |
| 5,507,280 | A | * | 4/1996 | Henkin et al. | 128/203.12 |
| 5,509,406 | A | * | 4/1996 | Kock et al. | 128/203.14 |
| 5,979,443 | A | * | 11/1999 | Dingley | 128/204.28 |
| 6,041,777 | A | * | 3/2000 | Faithfull et al. | 128/200.24 |
| 6,131,571 | A | * | 10/2000 | Lampotang et al. | 128/204.21 |
| 6,152,131 | A | * | 11/2000 | Heinonen | 128/204.23 |
| 6,298,848 | B1 | * | 10/2001 | Skog | 128/204.18 |
| 6,354,292 | B1 | * | 3/2002 | Fisher | 128/203.12 |
| 6,408,847 | B1 | * | 6/2002 | Nuckols et al. | 128/204.18 |
| 6,422,237 | B1 | * | 7/2002 | Engel et al. | 128/204.21 |

FOREIGN PATENT DOCUMENTS

| WO | PCT/SE96/00644 | 11/1996 |
|---|---|---|
| WO | PCT/CA97.00186 | 9/1998 |

* cited by examiner

Primary Examiner—Weilun Lo
Assistant Examiner—Teena Mitchell
(74) Attorney, Agent, or Firm—Stetina Brunda Garred & Brucker

(57) ABSTRACT

A portable isocapnia circuit and an isocapnia method. A breathing port of the circuit allows a subject to inhale and exhale. Connected to the breathing port, a bifurcate conduit has a first conduit branch and a second conduit branch. The first conduit branch has an atmospheric air inlet, from which the atmospheric air is provided for inhalation, an inspiratory check valve to allow a one-way flow of the atmospheric air, and an atmospheric air aspirator. The second conduit branch has a one-way expiratory check valve and a expiratory gas reservoir. A one-way check valve is used to interconnect the first and second conduit branch, from which the expiratory gas stored in the expiratory gas reservoir flows to the first conduit branch to mix with the atmospheric air when the minute ventilation exceeds the atmospheric air.

10 Claims, 3 Drawing Sheets

PORTABLE ISOCAPNIA CIRCUIT AND ISOCAPNIA METHOD

CROSS-REFERENCE TO RELATED APPLICATIONS

This application is a continuation-in-part of U.S. patent application Ser. No. 09/676,899 filed Oct. 2, 2000. This application claims priority to Canadian Application Serial No. 2,340,511 filed Mar. 21, 2001, which application claims priority to Canadian Application Serial No. 2,304,292 filed Mar. 31, 2000.

STATEMENT RE FEDERALLY SPONSORED RESEARCH/DEVELOPMENT (Not Applicable)

BACKGROUND OF THE INVENTION

The present invention relates to a portable isocapnia circuit and a method to set and stablize end tidal and arterial $PCO_2$ despite varying levels of minute ventilation.

Venous blood returns to the heart from the muscles and organs partially depleted of oxygen ($O_2$) and a full complement of carbon dioxide ($CO_2$). Blood from various parts of the body is mixed in the right side of the heart (resulting in the formation of mixed venous blood) and pumped into the lungs. In the lungs the blood vessels break up into a net of small vessels surrounding tiny lung sacs (alveoli). The vessels surrounding the alveoli provide a large surface area for the exchange of gases by diffusion along their concentration gradients. A concentration gradient exists between the partial pressure of $CO_2$ ($PCO_2$) in the mixed venous blood ($PvCO_2$) and that in the alveolar $PCO_2$. The $CO_2$ diffuses into the alveoli from the mixed venous blood from the beginning of inspiration until an equilibrium is reached between the $PvCO_2$ and the alveolar $PCO_2$ at some time during breath. When the subject exhales, the first gas that is exhaled comes from the trachea and major bronchi which do not allow gas exchange and therefore will have a gas composition similar to that of inhaled gas. The gas at the end of exhalation is considered to have come from the alveoli and reflects the equilibrium $CO_2$ concentration between the capillaries and the alveoli. The $PCO_2$ in this gas is the end-tidal $PCO_2$ ($PETCO_2$).

When blood passes the alveoli and is pumped to the left side of the heart to the arteries in the rest of the body, it is known as the arterial $PCO_2$ ($PaCO_2$). The arterial blood has a $PCO_2$ equal to the $PCO_2$ at equilibrium between the capillaries and alveoli. With each breath some $CO_2$ is eliminated from the lung and fresh air containing little or no $CO_2$ ($CO_2$ concentration is assumed to be 0%) is inhaled and dilutes the residual alveolar $PCO_2$, establishing a new gradient for $CO_2$ to diffuse out of the mixed venous blood into the alveoli. The flow of fresh gas in and out of the lungs each minute, or minute ventilation (V), expressed in L/min, is that required to eliminate the $CO_2$ brought to the lungs and maintain an equilibrium $PCO_2$ and ($PaCO_2$) of approximately 40 mmHg (in normal humans). When one produces more $CO_2$ (for example, as a result of fever or exercise), more $CO_2$ is produced and carried to the lungs. When $CO_2$ production is normal, the $PaCO_2$ falls if one increases the ventilation (hyperventilation). On the contrary, when $CO_2$ production remains normal, the $PaCO_2$ rises if one increases the ventilation (hypoventilation).

It is important to note that not all V contributes to elimination of $CO_2$. Some V goes air passage (trachea and major bronchi) and alveoli with little blood perfusing them, and thus contributes minimally to eliminating $CO_2$. This V is termed "dead space" ventilation and gas in the lung that has not participated in gas exchange with the blood is called "dead space" gas. That portion of V that goes to well-perfused alveoli and participates in gas exchange is called the alveolar ventilation (VA) and exhaled gas that has participated in gas exchange in the alveoli is termed "alveolar gas".

A method of accelerating the resuscitation of a patient has been disclosed in PCT application No. WO98/41266 filed by Joe Fisher. When the patient breathes at a rate such that his ventilation is less than or equal to the fresh gas flowing into the fresh glowing into the circuit, all of the inhaled gas is made up of fresh gas. When the patient's minute ventilation exceeds the fresh gas flow, the inhaled gas is made up of all of the fresh gas and the additional gas is provided by "reserve gas" consisting of fresh gas plus $CO_2$ such that the concentration of $CO_2$ in the reserve gas of about 6% has a $PCO_2$ equal to the $PCO_2$ in the mixed venous blood.

The limitation of the above method is that a source of reserve gas and its delivery apparatus must be supplied to pursue the method. The reserve gas must be at about 6% of $CO_2$ concentration substantially having a $PCO_2$ equal to that of mixed venous blood or about 46 mmHg. The portability is thus limited since a sufficiently long tubular structure, typically about 3 m, is required to prevent the atmospheric air from diffusing in and diluting the expired $CO_2$ concentrations. While climbing at high altitude, it would be very difficult to carry oxygen tanks and a long tubular expired gas reservoir. Another example of such a difficulty would be when preventing hyperventilation while ventilating with air in the course of resuscitating newborns and adults in out-of-hospital setting.

SUMMARY OF THE INVENTION

The invention provides a isocapnia circuit that maintains a constant $PCO_2$. A flexible container is used to replace the fresh gas reservoir bag used in the prior art. The flexible container is actively collapsed by the inspiratory effort of the patient during inspiration and passively expands during expiration, the atmospheric air is thus drawn into the flexible container and the circuit through a port. The expiratory reservoir is provided with a flexible bag so that the volume of expired gas rebreathed is displaced by collapse of the bag rather than entrainment of atmospheric air, thus preventing the dilution of $CO_2$ in the expired gas reservoir.

Therefore, the benefits of controlling the $PCO_2$ at a constant level are reaped and the expense and inconvenience of supplying fresh gas are not incurred. The compact nature of the isocapnia circuit makes its use practical outdoors, during physical activity and in remote environments. It has been determined that people living at high altitude such as mountaineers, miners, astronomical observatory personnel would benefit from preventing the $PCO_2$ level falling excessively as a result of the involuntary tendency to hyperventilate while they are at high altitude. It would also been determined that resuscitation of newborns with air has demonstrable advantages over resuscitation with oxygen if excessive decrease in $PCO_2$ can be prevented. This therefore was not contemplated in the prior art.

In the invention, the $PCO_2$ is controlled at a predetermined desired level without the need of gas from another source flowing into the circuit under pressure. The expired gas is stored to prevent dilution with atmospheric air such that alveolar portion of the expired gas is rebreathed in preference to dead space gas. The improved breathing circuit can be used to assist patients who are or run the risk of suffering the effects of high altitudes sickness, or who have suffered a cardiac arrest, or who have suffered from an interruption of blood flow to an organ or region of an organ and are at risk of suffering oxidative injury on restoration of blood perfusion as would occur with a stroke or heart attack or resuscitation of the newborn.

In the method of providing a constant $PCO_2$, atmospheric air is aspirated from an inspiratory side to a patient when the patient inhales through the inspiratory side. A gas exhaled by the patient is accumulated in an expiratory gas reservoir connected to an expiratory side, through which the patient exhale. The gas exhaled by the patient and stored in the expiratory gas reservoir is allowed flowing into the inspiratory side to mix with the aspirated atmospheric air when a minute ventilation of the patient exceeds the atmospheric air aspirated to the inspiratory side.

The above isocapnia circuit comprises a breathing port, through which a subject inhales and exhales; an inspiratory port, communicating to the breathing port with an inspiratory valve that allows air flowing to the breathing port and prevents air flowing from the breathing port to the inspiratory port, the inspiratory port having an atmospheric air aspirator to aspirate the atmospheric air therein; an expiratory port, communicating to the breathing port with an expiratory valve that allows air flowing from the breathing port to the expiratory port and prevents air flowing to the breathing port, the expiratory port having an expiratory gas reservoir to store a gas exhaled by the subject flowing across the expiratory valve; and a bypass conduit, communicating the inspiratory and expiratory ports with a bypass valve, the bypass valve allows a one-way flow of air from the expiratory port to the inspiratory port with a pressure differential applied thereto.

DETAILED DESCRIPTION OF THE INVENTION

Figure 1:
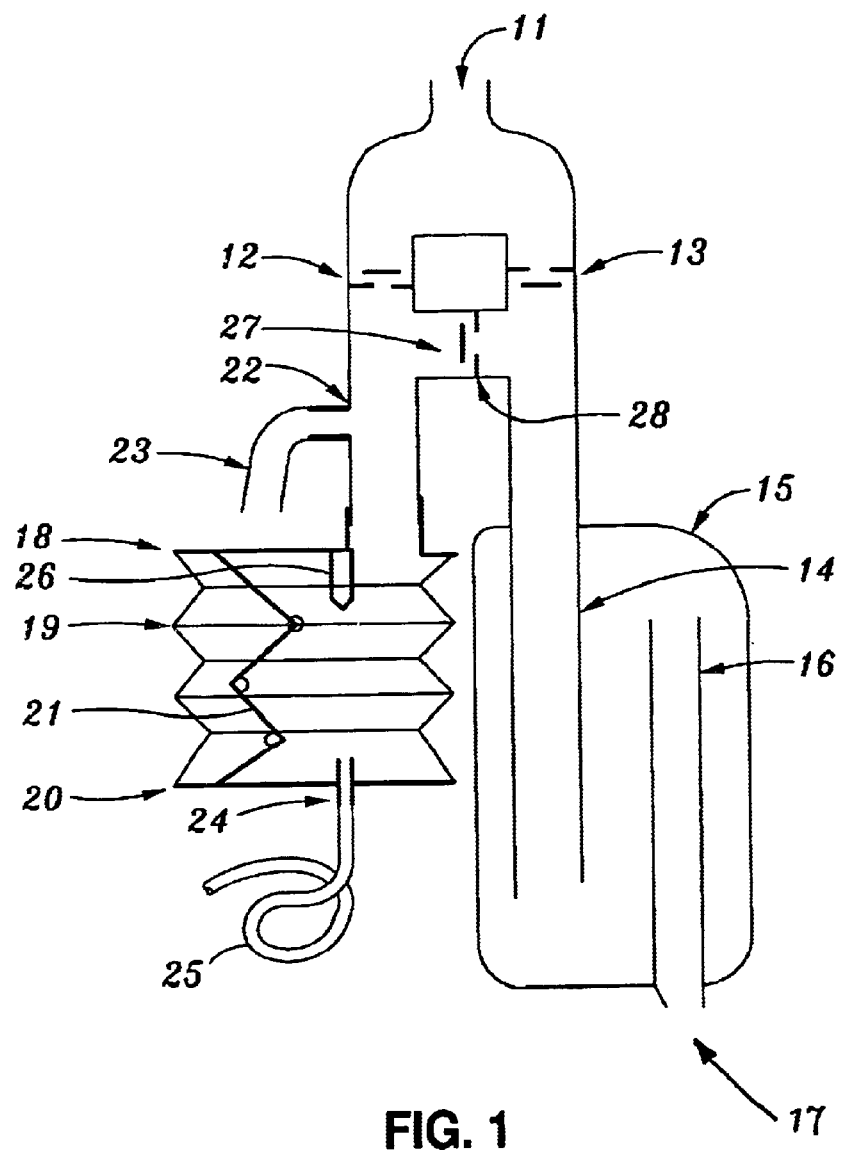
FIG. 1 schematically shows an isocapnia circuit in one embodiment of the invention.

FIG. 1 shows an air isocapnia circuit. The isocapnia circuit has a Y-piece 11, through one breathing port of which, the patient or subject breathes (inhales and exhales). In addition to the breathing port, the isocapnia circuit has another two ports in a form of two limbs of the Y-piece 11, and each of them comprises a one-way valve. One of the limbs with an inspiratory valve 12 functions as an inspiration port, while the other limb with an expiratory valve 13 functions as an expiration port. The inspiratory valve 12 directs gas to flow towards the patient when the patient makes an inspiratory effort, and acts as a check valve preventing flow in the opposite direction during exhalation. The expiratory valve 13 allows gas to exit the Y-piece 11 when the patient exhales, and also acts as a check valve to prevent flow towards the patient when the patient inhales.

Distal to the expiratory limb of the Y-piece 11, a large bore tubing termed "alveolar gas reservoir" 14 is attached. The alveolar gas reservoir 14 is contained in a pliable bag of about 3 L in volume. The pliable bag, named "expiratory gas reservoir bag" 15, has a proximal end sealed around a proximal end of the alveolar gas reservoir 14. The expiratory gas reservoir bag 15 further has another tubing called the "exhaust tubing" 16 situated at a distal end where the expired gas exits to atmosphere 17. Thus arranged, most of the exhaust tubing 16 is contained in the expiratory gas reservoir bag 15, and which is sealed to the circumference of the exhaust tubing 16 at its distal end. Preferably, the exhaust tubing 16 has a diameter smaller than that of the alveolar gas reservoir 14. In one embodiment, the alveolar gas reservoir 14 is about 35 mm in diameter, and has a length to provide a total volume of about or greater than 0.3 while being applied to an average (70 kg) adult. The inspiratory limb opens into a cylindrical container comprising a rigid proximal end plate 18, a collapsible plicate tube 19 extending distally from the circumference of the proximate end plate 18, and a distal end rigid plate 20 sealing the distal end of the collapsible plicate tube 19. When not in use, the collapsible plicate tube 19 is kept open by the gravitation of the distal end rigid plate 20, and/or by the force of a spring 21 attached on the collapsible plicate tube 19, and/or by intrinsic recoil of the plicate tubing 19. The inspiratory limb is also open to the atmosphere by means of a nozzle 22, to which a tube 23 is attached. The rigid plate 20 is open to a nozzle 24, to which another tube 25 is attached. The proximal end plate 18 has a protuberance 26 pointing at the tube 25 that is aligned with the internal opening of the distal end plate nozzle 24. The combination of the proximal end plate 18, the collapsible plicate tube 19, the distal end rigid plate 20, the spring 21, the inspiratory limb nozzle 22, the tube 23 attached to the nozzle 22, the distal end plate nozzle 24, the tube 25 attached to the distal end plate nozzle 24 and the protuberance 26 are in aggregate as am "atmosphere air aspirator (AAA)". A bypass conduit 27 is further included in the Y-piece 11 to connect the expiratory limb and the inspiratory limb. The opening of the bypass conduit 27 is preferably as close as possible to the expiratory valve 13. The bypass conduit 27 has a one-way valve 28 allowing flow from the expiratory limb to the inspiratory limb only. The one-way valve 28 of the bypass conduit 27 requires an opening pressure differential slightly greater than the pressure difference between the inspiratory limb pressure and atmospheric pressure that is sufficient to collapse the plicate tube 19. In this way, during inspiration, atmosphere air contained in the atmospheric air aspirator and the air being continuously aspirated into the inspiratory limb is preferentially drawn from the inspiratory manifold.

Considering the above isocapnia circuit without the spring 21, the nozzle 24 on the distal end plate 24, or the internally directed protuberance 26, each inspiration drawn initially from the atmospheric air aspirator collapses the plicate tube 19 and approximates the distal end plate 20 to the proximal end plate 18 when the patient begins to breathe. As long as the plicate tube 19 is partially collapsed, there is a constant sub-atmospheric pressure in the inspiratory limb of the isocapnia circuit. The sub-atmospheric pressure creates a pressure gradient that draws the atmospheric air into the inspiratory limb of the isocapnia circuit through the nozzle 22 and the tube 23. When the minute ventilation of the subject is equal to or less than the intended flow of atmospheric air into the aspirator, only atmospheric air is breathed. During exhalation, atmospheric air accumulates in the aspirator. During inhalation, inspired gas consist of the contents of the atmospheric air aspirator and the atmospheric air flowing into the inspiratory limb through the nozzle 23. When the minute ventilation of the subject exceeds the net flow of the atmospheric air into the isocapnia circuit, air is breathed for each breath until the atmospheric air aspirator is collapsed. Additional inspiratory efforts result in an additional decrease in gas pressure on the inspiratory side of the isocapnia circuit.

When the pressure differential across the valve 28 of the bypass conduit 27 exceeds its opening pressure, the one-way valve 28 opens and the exhaled gas is drawn back from the expiratory reservoir bag 15 into the inspiratory limb of the Y-piece 11 and hence to the patient. To the extent that the opening pressure of the valve 28 is close to the pressure generated by the recoil of the atmospheric air aspirator, there will be little change in the flow of atmospheric air into the isocapnia circuit during inspiration after the atmospheric air aspirator has collapsed. The last gas to be exhaled during the previous breath, termed "alveolar gas", is retained in the alveolar gas reservoir 14 and is the first gas to be drawn back into the inspiratory limb of the isocapnia circuit and inhaled (rebreathed) by the patient. After several breaths, the rest of the expired gas from the expiratory gas reservoir bag 15 contains mixed expired gas. The mixed expired gas from the expiratory gas reservoir bag 15 replace the gas drawn from the alveolar gas reservoir 14 and provides the balance of the inspired volume required to meet the inspiratory effort of the patient. The greater restriction in the diameter of the second tube, that is, the exhaust tubing 16, than in the alveolar gas reservoir 14 results in the gas being drawn into the alveolar gas reservoir 14 being displaced by the collapse of the expiratory gas reservoir bag 15 in preference to drawing air from the ambient atmosphere. The exhaust tubing in the expiratory reservoir bag 16 provides a route for exhaust of expired gas and acts as a reservoir for that volume of atmospheric air diffusing into the expiratory reservoir bag through the distal opening, tending to keep such atmospheric air separate from the mixed expired gas contained in the expiratory gas reservoir bag 15.

During exhalation and all of inhalation until the collapse of the atmospheric gas aspirator, the flow of atmospheric air into the circuit will remain constant. However, after the atmospheric air aspirator collapses, the pressure gradient will increase. The effect of the increase in total flow will depend on the difference between the opening pressure of the bypass valve 28 and the recoil pressure of the atmospheric air aspirator times the fraction of the respiratory cycle when the atmospheric air aspirator is collapsed. If the fraction of the respiratory cycle when the atmospheric air aspirator is collapsed is great, as when there is a very great excess minute ventilation above the rate of atmospheric air aspiration, the atmospheric air aspirator can be modified adding a second port for air entry at, for example, the distal end plate nozzle 24. As a result, the total flow from the two ports provides the desired total flow of air into the circuit under the recoil pressure of the atmospheric air aspirator. When the atmospheric air aspirator collapses on inspiration, the second port 24 is occluded by the protuberance 26. The remaining port, that is, the nozzle 22, provides a greater resistance to air flow to offset the greater pressure gradient being that gradient required to open the bypass valve 28.

In the above embodiment, it is assumed that the gravitation acting on the distal plate 20 provides the recoil pressure to open the atmospheric air aspirator. The disadvantage to this configuration is that the distal end plate 20 must be heavy enough to generate the sub-atmospheric pressure. This may be too heavy to be supported by attachment to a face mask strapped to the face. Furthermore, movement such as walking or running or spasmodic inhalation will cause variations in the pressure inside the atmospheric air aspirator and hence variation in flow of air into the atmospheric air aspirator. In such cases, it is better to minimize the mass of the distal end plate 20 and use a different type of motive force to provide recoil symbolized by the spring 21.

Figure 2:
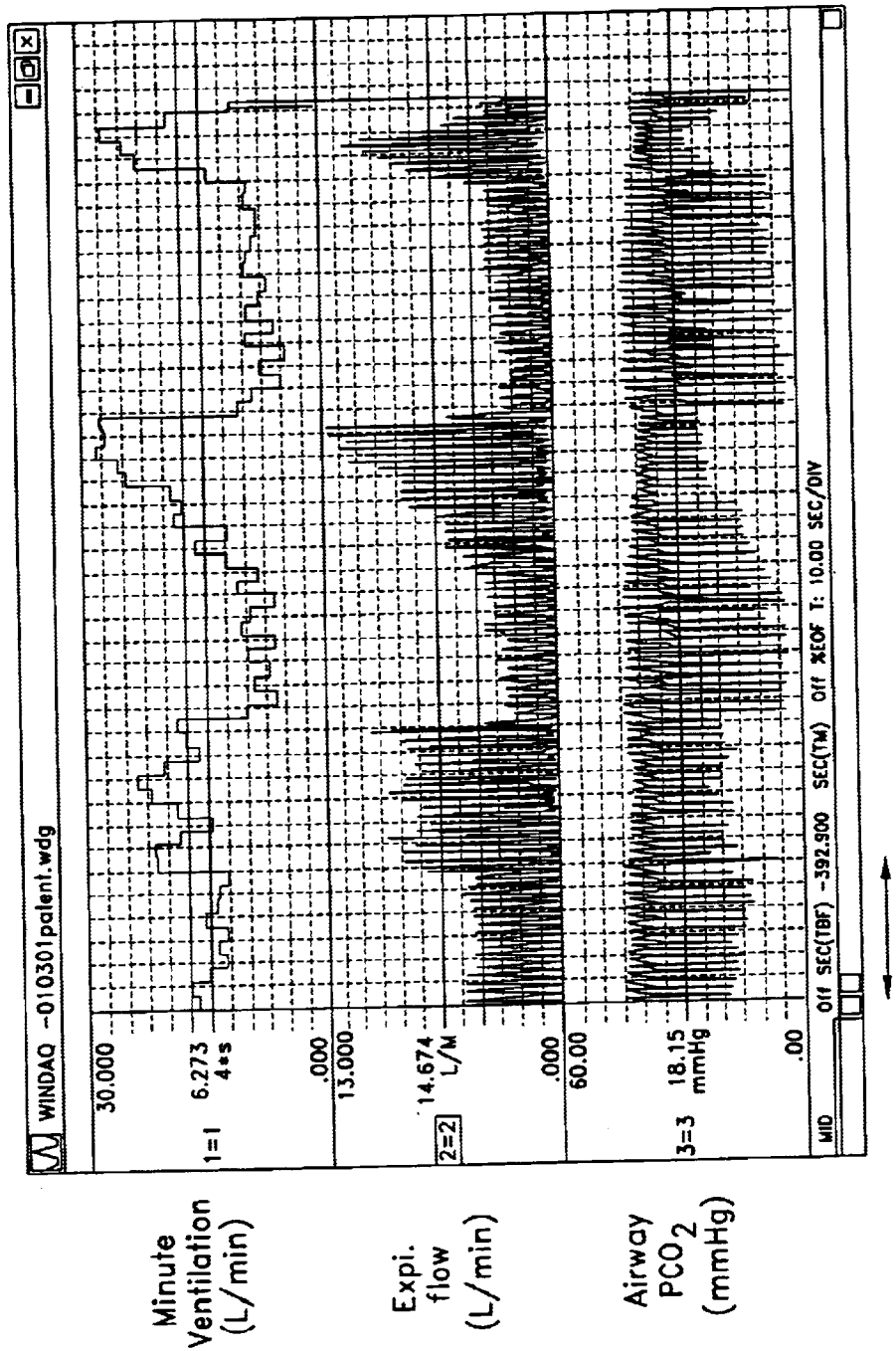
FIG. 2 and FIG. 3 show data resulting from the method and the circuit applied in the invention.
Figure 3:
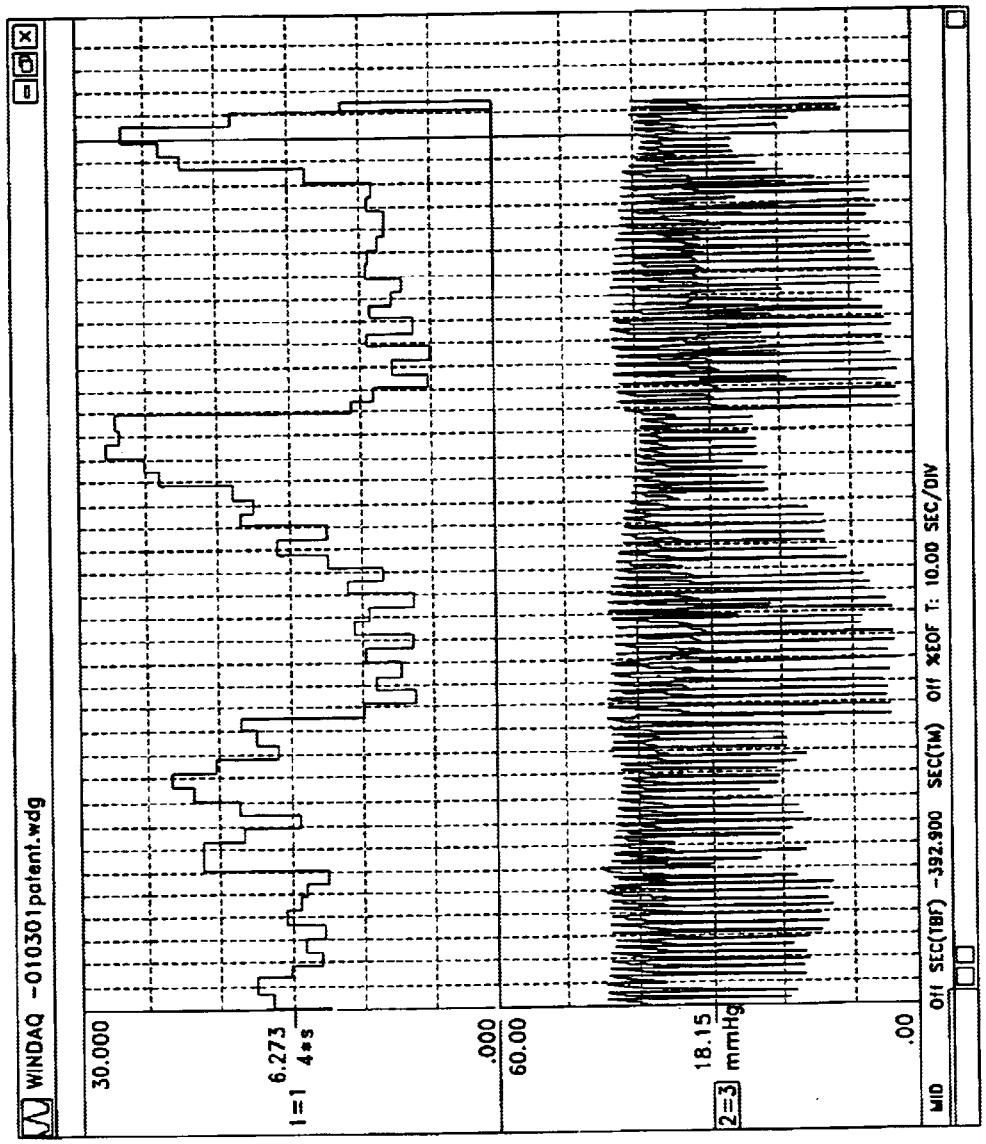

The advantages of the isocapnia circuit and method provided by the invention in terms of the operation and portability are clearly evident from the data charted in FIGS. 2 and 3, in which levels of minute ventilation, expired gas flow and airway $PCO_2$ are compared.

Preferably, the above isocapnia circuit is installed in a case to render it fully portable. This case may include the appropriate number of capped ports to allow proper set up and use of the isocapnia circuit.

The operation of the above isocapnia circuit is described as follows. When the minute ventilation for the patient breathing through the breathing port is equal to the rate of atmospheric air aspirated into the isocapnia circuit, for example, 5 L per minute, the atmospheric air enters the breathing port from the first conduit branch, that is, the inspiratory limb, at a predetermined rate, preferably, 5 L per minute and is exhaled through the second conduit branch, that is, the expiratory limb, at a rate of preferably 5 L per minute. The exhaled gas travels down to the expiratory gas reservoir bag 25. When the minute ventilation exceeds the aspirated atmospheric air, the patient inhales the expiratory gas retained in the expiratory gas reservoir bag 25. The expiratory gas passes through the bypass valve 28 to the inspiratory limb to make up the shortfall of the atmospheric air. In this way, the $PCO_2$ is maintained with a constant value even when the minute ventilation increases.

To maintain the constant value of $PCO_2$, it is important to have atmospheric air aspirator depleted of gas first until it is just empty at the end of an inhalation cycle. Once the minute ventilation is increased, the increased breathing effort will further decrease the sub-atmospheric pressure in the inspiratory limb and open the bypass valve 28 to allow the expiratory gas supplied as a part of the breathing gas during the entire breathing cycle.

During resuscitation of an asphyxiated newborn or an adult suffering a cardiac arrest, the blood flow through the lungs is remarkably slow during resuscitation attempts. Even normal rates of ventilation may result an excessive elimination of $CO_2$ from the blood. As the blood reaches brain, the low $PCO_2$ may constrict the blood vessels and limit the potential blood flow to the ischemic brain. By attaching the isocapnia circuit provided by the invention to the gas inlet port of a resuscitation bag and diverting all expiratory gas to the expiratory gas reservoir bag, the decrease of $PCO_2$ would be limited.

The above isocapnia circuit can be applied to enhance the results of a diagnostic procedure or a medical treatment including the following steps. The circuit without a source of forced gas glow and capable of organizing exhaled gas is used. With the circuit, preferential rebreathing of alveolar gas in preference to dead space gas is provided when the patient is ventilating at a rate greater than the rate of atmospheric air aspirated, and when inducing hypercapnia is desired. By decreasing the rate of aspirated atmospheric air, a corresponding increase in rebreathed gas is passively provided to prevent the $PCO_2$ level of arterial blood from dropping despite increase in minute ventilation. The step of inducing hypercapnia is continued until the diagnostic or medical therapeutic procedure is complete. The results of the diagnostic or medical procedure are thus enhanced by carrying out the method in relation to the results of the procedure had the method not been carried out. Examples of such procedures include MRI or preventing spasm of brain vessels after brain hemorrhage, radiation treatments or the like.

The invention can also be applied to treat or assist a patient, preferably human, during a traumatic event characterized by hyperventilation. A circuit that does not required a source of forced gas flow, in which alveolar ventilation is equal to the rate of atmospheric air aspirated and increases in alveolar ventilation with increases in minute ventilation is prevented, is provided. The circuit, for example, the isocapnia circuit as described above, is capable of organizing exhaled gas provided to the patient preferential rebreathing alveolar gas in preference to dead space gas following ventilating the patient at a rate of normal minute ventilation, preferably approximately 5 L per minute. When desired, hypercapnia is induced to increase arterial $PCO_2$ and prevent the $PCO_2$ level of arterial blood from dropping. The normocapnia is maintained despite the ventilation is increased until the traumatic hyperventilation is complete. As a result, the effects of hyperventilation experienced during the traumatic event are minimized. This can be applied when the mother is in labor and becomes light headed or the baby during the delivery is effected with the oxygen delivery to its brain being decreased as a result of contraction of the blood vessels in the placenta and fetal brain. A list of circumstances in which the method enhancing the diagnostic procedure results or the experience of the traumatic even are listed below.

Applications of the method and circuit includes:
1) Maintenance of constant $PCO_2$ and inducing changes in $PCO_2$ during MRI.
2) Inducing and/or marinating increased $PCO_2$:
   a) to prevent or treat shivering and tremors during labor, post-anesthesia, hypothermia, and certain other pathological states;
   b) to treat fetal distress due to asphyxia;
   c) to induce cerebral vasodilatation, prevent cerebral vasospasm, and provide cerebral protection following subarachnoid hemorrhage cerebral trauma and other pathological states;
   d) to increase tissue perfusion in tissues containing cancerous cells to increase their sensitivity to ionizing radiation and delivery of chemotherapeutic agents;
   e) to aid in radiodiagnostic procedures by providing contrast between tissues with normal and abnormal vascular response; and
   f) protection of various organs such as the lung, kidney and brain during states of multi-organ failure.
3) Prevention of hypocapnia with $O_2$ therapy, especially in pregnant patients.
4) Other applications where $O_2$ therapy is desired and it is important to prevent the accompanying drop in $PCO_2$.

When minute ventilation is greater than or equal to the rate of atmospheric air aspirated, the above-mentioned preferred circuit ensures that the patient receives all the atmospheric air aspirated into the circuit independent of the pattern of breathing since atmospheric air alone enters the fresh gas reservoir, and exhaled gas enters its own separate reservoir and all the aspirated air is delivered to the patient during inhalation before rebreathed exhaled gas. The atmospheric air aspirator is large enough not to fill to capacity during a prolonged exhalation when the total minute ventilation exceeds the rate of atmospheric air aspiration ensuring that under these circumstances atmospheric air continues to enter the circuit uninterrupted during exhalation. The preferred circuit prevents rebreathing at a minute ventilation equal to the rate of air being aspirated into the atmospheric air aspirator because the check valve in the interconnecting conduit does not open to allow rebreathing of previously exhaled gas unless a sub-atmospheric pressure less than that generated by the recoil of the aspirator exists on the inspiratory side of the conduit of the circuit. The circuit provides that after the check valve opens, alveolar gas is rebreathed in preference to dead space gas because the interconnecting conduit is located such that exhaled alveolar gas contained in the tube conducting the expired gas into the expiratory reservoir bag will be closest to it and dead space gas will be mixed with other exhaled gases in the reservoir bag. The exhaled gas reservoir is preferably sized at about 3 L which is well excess of the volume of an individual's breath. When the patient inhales gas from the reservoir bag, the reservoir bag collapses to displace the volume of gas extracted from the bag, minimizing the volume of atmospheric air entering the bag.

The basic approach of preventing a decrease in $PCO_2$ with increase ventilation is briefly described as follows. Only breathing the fresh gas contributes to alveolar ventilation (VA) which establishes the gradient for $CO_2$ elimination. All gas breathed in excess of the fresh gas entering the circuit, or the fresh gas flow, is rebreathed gas. The closer the partial pressure of $CO_2$ in the inhaled gas to that of mixed venous blood ($PvCO_2$), the less the effect on $CO_2$ elimination. The relationship between the alveolar ventilation, minute ventilation (V) and $PCO_2$ of rebreathed gas is $VA=FGF+(V-FGF)(PvCO_2-PCO_2$ of exhaled gas$)/PvCO_2$ where FGF stands for the fresh gas flow. With respect to this circuit, the fresh gas flow is equivalent to the rate of atmospheric air aspirated into the atmospheric air aspirator.

It is clear from this equation that as the $PCO_2$ of the exhaled gas approaches that of the mixed venous blood, the alveolar ventilation is determined only by the fresh gas flow and not the minute ventilation.

As one exhales, the first gas to exit the mouth comes from the tracheas where no gas exchange has occurred. The $PCO_2$ of this gas is identical to that of the inhaled gas and is termed as "dead space gas". The last gas to exit the mouth originates from the alveoli and has had the most time to equilibrate with mixed venous blood, has a $PCO_2$ closest to that of mixed venous blood and is termed as "alveolar gas". Gas exhaled between these two periods has a $PCO_2$ intermediate between the two concentrations. The equation cited above explains why rebreathing alveolar gas would be the most effective in maintaining the $PCO_2$ at a constant level when minute ventilation increases.

Accordingly, in the above isocapnia circuit:
1. All of the fresh gas, in the form of atmospheric air, is inhaled by the subject and contributes to alveolar ventilation when minute ventilation is equal to or exceeds the rate of atmospheric air aspirated into the AAA.
2. The alveolar gas is preferentially rebreathed when minute ventilation exceeds the fresh gas flow.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:
1. A method of providing constant $PCO_2$ to a patient wearing a breathing port having an inspiratory side and an expiratory side, the method comprising:
   aspirating atmospheric air from the inspiratory side to a patient when the patient inhales through the inspiratory side;
   accumulating the gas exhaled by the patient in an expiratory gas reservoir connected to the expiratory side, through which the patient exhales; and
   allowing the gas exhaled by the patient and stored in the expiratory gas reservoir to flow into the inspiratory side to mix with the aspirated atmospheric air when a minute ventilation of the patient exceeds the atmospheric air aspirated to the inspiratory side.

2. An isocapnia circuit, comprising:

a breathing port, through which a subject inhales and exhales;

an inspiratory port, communicating to the breathing port with an inspiratory valve that allows air flowing to the breathing port and prevents air flowing from the breathing port to the inspiratory port, the inspiratory port having an atmospheric air aspirator to aspirate the atmospheric air therein;

an expiratory port, communicating to the breathing port with an expiratory valve that allows air flowing from the breathing port to the expiratory port and prevents air flowing to the breathing port, the expiratory port having an expiratory gas reservoir to store gas exhaled by the subject flowing across the expiratory valve; and a bypass conduit, communicating the inspiratory and expiratory ports with a bypass valve, the bypass valve allows a one-way flow of air from the expiratory port to the inspiratory port with a pressure differential applied thereto.

3. The isocapnia circuit as claimed in claim 2, wherein the expiratory gas reservoir further comprises:

alveolar gas reservoir, connecting the expiratory port and the expiratory gas reservoir, around one end of which the expiratory gas reservoir being sealed, the alveolar gas reservoir has the other end extending into the expiratory the gas reservoir; and an exhaust tubing, from which the gas within the expiratory gas reservoir exhausts.

4. The isocapnia circuit as claimed in claim 3, wherein the alveolar gas reservoir has a diameter larger than that of the exhaust tubing.

5. The isocapnia circuit as claimed in claim 2, wherein the expiratory gas reservoir has a capacity in excess of a volume of a user's breath.

6. The isocapnia as claimed in claim 2, wherein the atmospheric air aspirator further comprises:

a first end plate, where the inspiratory port opens to;

a collapsible plicate tube;

a second end rigid plate, with the collapsible tube accommodated between the first end plate and the second end rigid plate;

an inspiratory port nozzle located between the inspiratory valve and the first end plate, where the inspiratory port opens to the atmospheric air;

a first tube, attached to the inspiratory port nozzle;

an end plate nozzle, from which the collapsible tube opens to the atmospheric air;

a second tube, attached to the end plate nozzle; and a protuberance, attached on the first end plate and pointing at the end plate nozzle to close an opening of the collapsible plicate tube while collapsed.

7. The isocapnia circuit as claimed in claim 6, wherein the atmospheric air aspirator further comprises a spring to recoil the collapsible plicate tube.

8. An isocapnia circuit, comprising:

a breathing port, through which a subject exhales and inhales;

a bifurcated conduit adjacent and connected to the breathing port, including a first conduit branch and a second conduit branch, the first conduit branch further including:

an atmospheric air inlet; and an inspiratory check valve located between the breathing port and the atmospheric air inlet and an expiratory check valve located in the second conduit branch, wherein the inspiratory and expiratory check valves are both one-way passage valves;

an atmospheric air aspirator connected to the first conduit branch, having a collapsible container formed to recoil to an open position;

a flexible expiratory gas reservoir, having an entrance tubing through which the flexible expiratory gas reservoir is connected to the second conduit, and an exit tubing open to the atmospheric air; and a bypass conduit, communicating between the first and the second conduit branches, having a one-way check valve therein.

9. An isocapnia circuit, comprising:

a breathing port, through which a subject exhales and inhales;

a bifurcated conduit adjacent and connected to the breathing port, including a first conduit branch and a second conduit branch, the first conduit branch further including:

a fresh gas inlet; and a one way inspiratory check valve, located between the breathing port and the fresh gas inlet, the second conduit branch further including a one way expiratory check valve located between the breathing port and an exhaust outlet;

an atmospheric air aspirator connected to the first conduit branch, having a collapsible container formed to recoil to an open position;

a flexible expiratory gas reservoir, having an entrance tubing through which the flexible expiratory gas reservoir is connected to the second conduit, and an exit tubing open to the atmospheric air; and a bypass conduit communicating between the first and the second conduit branches, having a one-way check valve therein, and responding to a predetermined pressure, to draw expired gas into the first branch to maintain a substantially constant $PCO_2$ level in the subject independent of minute ventilation.

10. The circuit of claim 9 wherein said atmospheric air aspirator further comprises a second port for fresh gas entry.

* * * * *